(12) United States Patent
Shaw et al.

(10) Patent No.: US 8,758,703 B2
(45) Date of Patent: Jun. 24, 2014

(54) DEVICE AND METHOD FOR DILUTING A SAMPLE

(75) Inventors: Philip Neil Shaw, Winsford (GB); Philip Marriott, Winsford (GB)

(73) Assignee: Thermo Fisher Scientific Inc., Waltham, MA (US)

( * ) Notice: Subject to any disclaimer, the term of this patent is extended or adjusted under 35 U.S.C. 154(b) by 245 days.

(21) Appl. No.: 13/111,588

(22) Filed: May 19, 2011

(65) Prior Publication Data

US 2011/0290996 A1    Dec. 1, 2011

Related U.S. Application Data

(62) Division of application No. 10/524,382, filed as application No. PCT/GB03/03569 on Aug. 14, 2003, now Pat. No. 7,998,434.

(30) Foreign Application Priority Data

Aug. 14, 2002    (GB) .................................. 0218946.2

(51) Int. Cl.
    *F04B 53/00*    (2006.01)
(52) U.S. Cl.
    USPC ........... 422/501; 422/509; 422/514; 436/179; 436/180; 250/288
(58) Field of Classification Search
    USPC .................. 422/501, 509, 514; 436/179, 180; 250/288
    See application file for complete search history.

(56) References Cited

U.S. PATENT DOCUMENTS

| 4,245,509 A | 1/1981 | Mody et al. |
|---|---|---|
| 4,441,374 A | 4/1984 | Suzuki |
| 4,684,251 A | 8/1987 | Brouwer et al. |
| 4,790,454 A | 12/1988 | Clark et al. |
| 4,794,806 A | 1/1989 | Nicoli et al. |
| 4,804,519 A | 2/1989 | Sainz et al. |
| 4,836,038 A | 6/1989 | Baldwyn |

(Continued)

FOREIGN PATENT DOCUMENTS

| EP | 0118815 | 9/1984 |
|---|---|---|
| EP | 0229599 | 7/1987 |

(Continued)

OTHER PUBLICATIONS

Japanese Patent Office, Examiner's Report of Reconsideration, no date, Application No. 528676/2004, 2 pages.

(Continued)

*Primary Examiner* — Brian R Gordon
*Assistant Examiner* — Shogo Sasaki
(74) *Attorney, Agent, or Firm* — Haynes and Boone, LLP

(57) ABSTRACT

The present invention provides a pump device 50 which is usable to dilute a sample 52 before analysis. A first pump 54 pumps the sample to a mixing region 58 where it mixes with a diluent 66. A second pump 64 pumps the diluted sample to the analysis instrument. The flow of the diluent to the mixer is equal to the difference of the flow of the sample to the mixer and the flow of the diluted sample to the instrument. Pumps 54 and 64 are independently controllable by a controller unit which is arranged so that data from the instrument can be used to determine the dilution factor of the sample. Thus, the controller can control this dilution factor in real time, upon receipt of such data from the instrument, by change either one of (or both) the pump's flow rate.

26 Claims, 6 Drawing Sheets

(56) References Cited

U.S. PATENT DOCUMENTS

| | | | |
|---|---|---|---|
| 5,007,297 | A | 4/1991 | Sommer |
| 5,080,866 | A | 1/1992 | Petty et al. |
| 5,221,521 | A | 6/1993 | Hashizume et al. |
| 5,237,385 | A | 8/1993 | Pfeil et al. |
| 5,355,214 | A | 10/1994 | Hammer |
| 5,393,673 | A | 2/1995 | Gjerde et al. |
| 5,414,259 | A | 5/1995 | Kingston |
| 5,624,846 | A | 4/1997 | Hayashibe et al. |
| 5,646,727 | A | 7/1997 | Hammer et al. |
| 5,783,450 | A | 7/1998 | Yoshida et al. |
| 5,928,953 | A | 7/1999 | Kallback |
| 6,079,313 | A | 6/2000 | Wolcott et al. |
| 6,211,956 | B1 | 4/2001 | Nicoli |
| 6,324,924 | B1 | 12/2001 | Peterson |
| 6,974,951 | B1 | 12/2005 | Kingston |
| 2002/0011437 | A1 | 1/2002 | Kaito et al. |
| 2006/0104827 | A1 | 5/2006 | Shaw et al. |
| 2006/0127237 | A1 | 6/2006 | Shaw et al. |

FOREIGN PATENT DOCUMENTS

| | | |
|---|---|---|
| EP | 0351995 | 1/1990 |
| EP | 0800073 | 10/1997 |
| GB | 2081897 | 2/1982 |
| JP | 52119502 | 10/1977 |
| JP | 5657954 | 5/1981 |
| JP | 610046233 | 3/1986 |
| JP | 1104334 | 4/1989 |
| JP | 116788 | 1/1999 |
| JP | 11326302 | 11/1999 |
| JP | 2000292318 | 10/2000 |
| WO | WO-87/03092 | 5/1987 |
| WO | WO-98/22797 | 5/1998 |
| WO | WO 02/060565 A1 | 8/2002 |
| WO | WO-2004/017046 | 2/2004 |

OTHER PUBLICATIONS

Australian Patent Office, Examiner's report dated May 6, 2008, Application No. 2003255795; Applicant's response dated Jun. 9, 2009, 35 pages.

Chinese Patent Office, Office Action dated Apr. 6, 2007, Application No. 03819262.4, Applicant's response dated Jan. 3, 2008, 49 pages.

Chinese Patent Office, Office Action dated Sep. 26, 2008, Application No. 03819262.4, Applicant's response dated Dec. 4, 2008, 29 pages.

Japanese Patent Office, Office Action, Application No. 2004-528676, Applicant's response, 44 pages.

Sobodnik, et al., "Integrated System for On-Line Gas and Liquid Chromatography with a Single Mass Spectrometric Detector for the Automated Analysis of Environmental Samples," Journal of Chromatography A, Elsevier Science, NL, vol. 730, No. 1, Apr. 12, 1996, pp. 353-371, XP004039249, ISSN: 0021-9673.

Great Britain Search Report for GB0218949.6 dated Feb. 14, 2003.

Patent Cooperation Treaty Search Report PCT/GB03/03564, dated Nov. 24, 2003.

Huang, C., et al., "Automated On-Line Sample Pretreatment System for the Determination of Trace Metals in Biological Samples by Inductively Coupled Plasma Mass Spectrometry," Analytical Chemistry, American Chemical Society, vol. 69, No. 19, Oct. 1, 10997, pp. 3930-3939, XP002055756, ISSN: 0003-2700.

Japanese Patent Office, Decision to Refuse and Appeal Brief, Application No. 2004-528676, 13 pages.

UK patent application for GB2081897 filed Jul. 23, 1981, 10 pages.

Unicam, "Design Considerations for an in Line Dilution Accessory for Flame Atomic Absorption Spectrometry" SOLAAR Series Atomic Absorption Spectrometers (11 pages), 2013.

Fluka Analytical, "Inorganic Trace Analysis" Sigma-Aldrich Co., 2012 (12 pages).

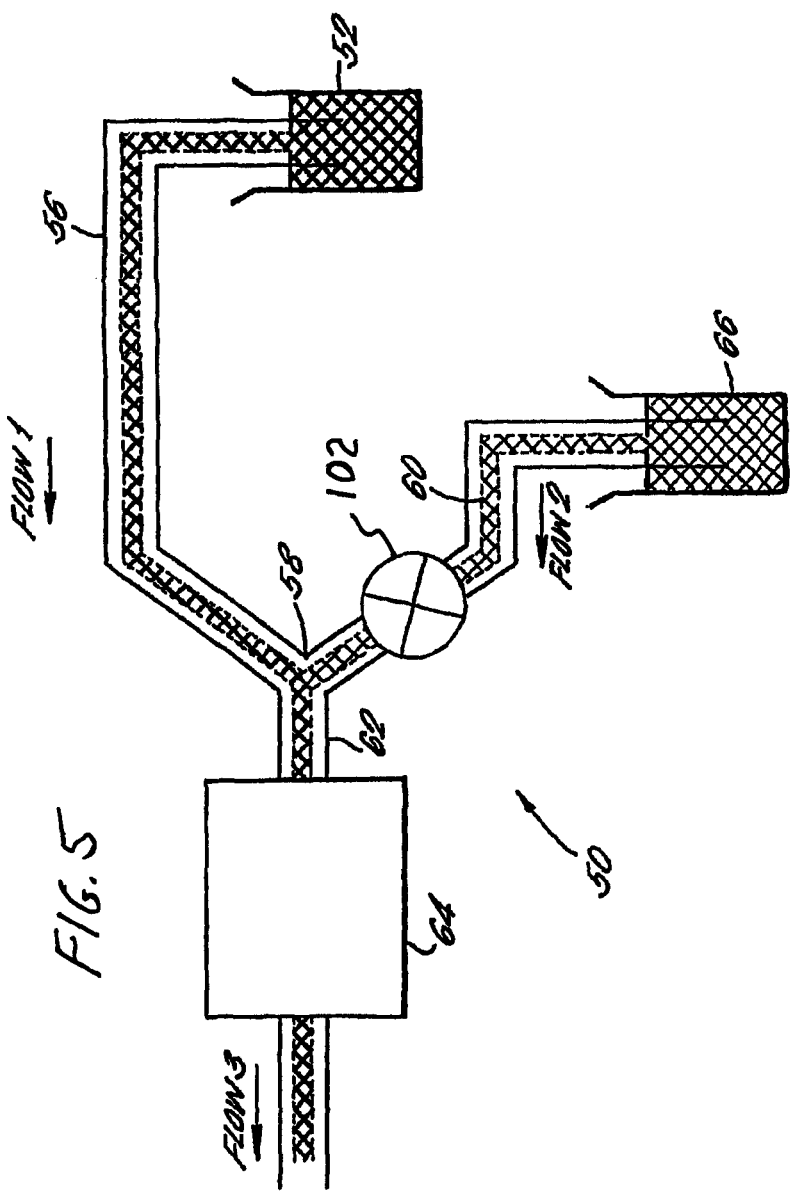

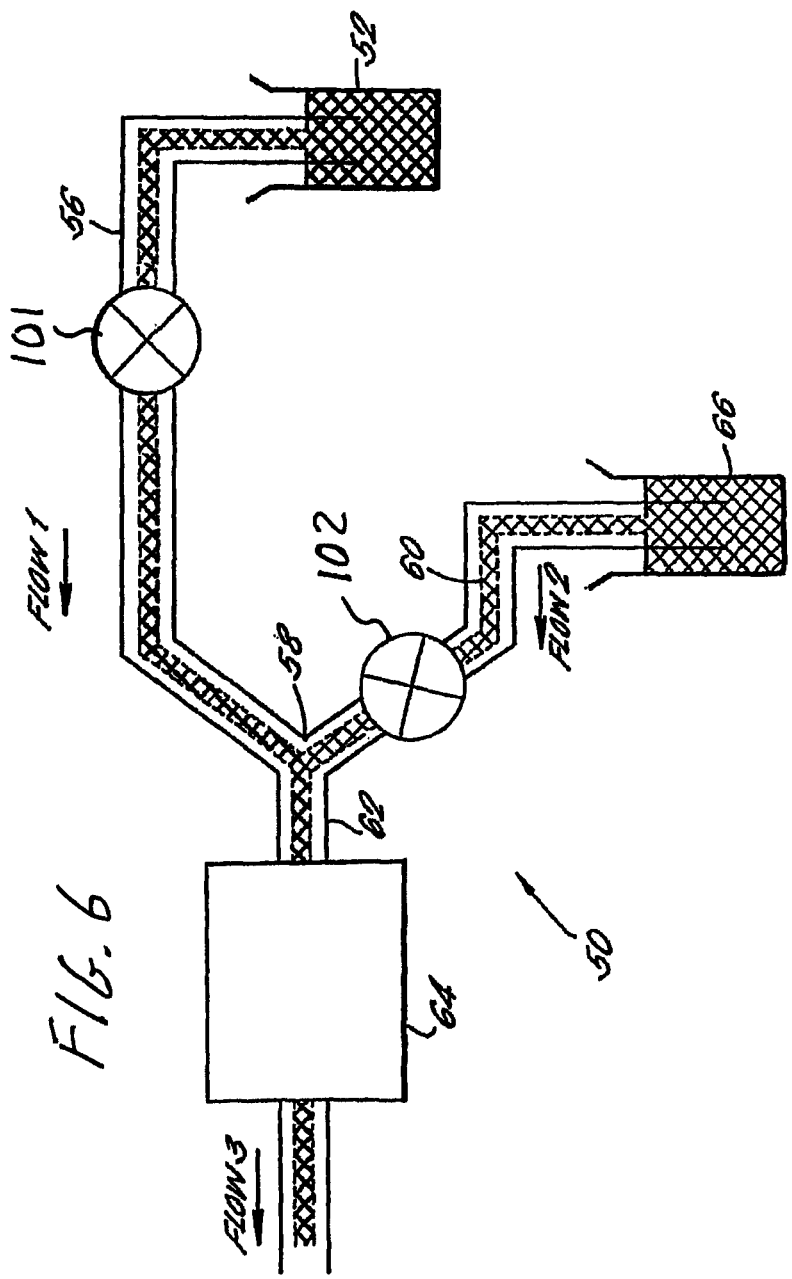

DEVICE AND METHOD FOR DILUTING A SAMPLE

PRIOR APPLICATIONS

This application is a divisional application of U.S. patent application Ser. No. 10/524,382 filed Sep. 30, 2005, now U.S. Pat. No. 7,998,434 issued Aug. 16, 2011, which claims the benefit of Patent Cooperation Treaty Application Number PCT/GB2003/003569, filed Aug. 14, 2003, which claims priority from Great Britain Application Number 0218946.2, filed Aug. 14, 2002, all of which are incorporated herein by reference. This invention relates to U.S. patent application Ser. No. 10/524,706 with an International Filing Date of Aug. 14, 2003, entitled, "Method And Apparatus for Pumping And Diluting A Sample" assigned to a common assignee.

FIELD OF THE INVENTION

This invention relates to a method and apparatus for diluting a sample before performing mass spectrometry on the sample.

The invention is described herein with reference to liquid samples which require dilution before they are analysed in a mass spectrometer. However, the invention is not limited to liquid samples and can equally apply to dissolved or suspended samples.

DESCRIPTION OF THE RELATED ART

Analysis equipment for analysing trace elements in liquids have a limited capability of measuring samples which contain relatively high levels of dissolved solid material, or matrix (such as $CaCO_3$ or dissolved salts in water, or the like). The trace elements of interest to the user are often only a few parts per billion, or lower, whilst the matrix can be many parts per million, or higher. Such high levels of matrix can have undesirable effects on the analytical equipment, such as deposition of materials on orifices, glassware, or ion optical elements, unless the sample is appropriately diluted.

Inductively coupled plasma mass spectrometers (ICP-MS) typically require a total dissolved solid level of less than 2000 mg/l to avoid this so-called swamping effect. The dissolved solids which are deposited on components within the instrument, for example on the cones which sample the plasma and skim off a portion of the supersonic jet, significantly reduces the reliability of a test result and the results of any other subsequent test. If deposition of materials occurs, the instrument has to be thoroughly cleaned before accurate testing can resume.

Test laboratories are often required to analyse many samples quickly where the matrix content of each sample varies widely. Typically, the user would wish to dilute each sample by a certain amount to determine the analytes present in each sample, and whether the sample can be analysed undiluted. If dilution is required, this initial test provides an indication of the dilution factor necessary to bring the total dissolved solids down to a level tolerated by the instrument.

Such manual intervention is too cumbersome, time consuming and costly if many samples per day require analysis. Presently, samples which introduce too great a loading of dissolved solids for the instrument to cope with are re-analysed once the analyser has been cleaned. Analysis must cease for instrument cleaning, and samples inadvertently analysed after contamination has occurred must be re-analysed. These additional steps require considerable operator intervention. Such a limit to the throughput of samples is undesirable and operator intervention is costly.

Automated dilution systems have been used previously and, referring to FIG. 1, such an automated system 10 known in the art is shown in highly schematic form. A sample 12 is drawn from a container by a sample pump 14 to a mixing tube 16. Similarly, a diluent 18 is drawn by a diluent pump 20 to the mixing tube 16 from a separate diluent container. The sample is diluted in the mixing tube where it is completely mixed with diluent. An instrument pump 22 draws the diluted sample from the mixing tube and into the instrument or analyser, not shown in FIG. 1.

Both the sample and diluent pumps have to be able to maintain accurately flow rates to ensure the sample is diluted precisely. If the dilution is not maintained to a known level and within a relatively tight tolerance, the accuracy of the analysis results may be unacceptable. Likewise, the instrument flow must be maintained at an accurate flow rate to ensure the diluted sample is pumped to the analyser's input at a known, controllable rate. Thus, all the pumps (and their associated flow rates) need to be controlled accurately to maintain accurate test results.

Presently, peristaltic pumps are used to pump the sample, diluent and diluted sample through the dilution system. Typically, dilutions ratios of 50:1 of diluent to sample are used for mass spectroscopy. Hence, the diluent pump rate is typically fifty times greater than the sample pump rate. Peristaltic pumps have a limited range of flow rates and the sample and diluent pumps often operate at the extremes of their flow rate range. Also, the limited flow rate for peristaltic pumps limits the dilution factor by which the sample can be diluted.

The rate at which the diluted sample enters the instrument (not shown) depends on the type of instrument being used but is relatively low and typically a few millilitres per minute. Typically, the combined flow rates of the sample and diluent pumps exceeds the instrument pump flow rate. This is because all the pumps have a relatively similar range of flow rates in which they can operate. Thus, for example, at dilution factors greater than ten, the dilution pump 20 must be operating at a high flow rate which typically exceeds the acceptable flow rate of the analysis instrument. It is, therefore, necessary to provide a waste outlet 24 to prevent build up of pressure in the system; excess diluted sample not pumped to the instrument flows to a waste container 26. At high dilution factors, the solution flowing to waste can exceed the solution entering the analyser by as much as a factor of fifty. Materials in the waste container are discarded and, since high quality diluent necessary for accurate test results is relatively expensive, this wastage is an additional economic burden on test laboratories.

Other types of pumps, such as syringe pumps can also used. Syringe pumps require the syringe to draw up the fluid (be it the sample or diluent) before it is pumped to the analysis instrument. A series of valves is therefore required to ensure the correct flow of fluid through the system. The additional time required to draw the fluid into the syringe limits the laboratory's (or analysis instrument's) ability to test many samples over a period of time. Furthermore, the time required to control the valves further limits the throughput of test samples, and extra control algorithms may be necessary for the system controller to control the valves, further increasing system complexity.

A pumping system similar to the ones described above is disclosed in U.S. Pat. No. 5,007,297 (Pacific Scientific Company).

Another automated pumping system 28 known in the art is shown in FIG. 2 in highly schematic form. Sample 29 is pumped along a first pipe 30 by a syringe pump 31 to fill the syringe (not shown). A valve 32 is closed to prevent fluid entering the syringe from the pump discharge pipe 33. When the pump is charged with an appropriate amount of sample, the valve is opened and the syringe plunger driven at a constant rate to provide a flow of sample along pipe 33 in the general direction indicated by arrow Z. A one way valve in the pump (not shown) prevents the sample from flowing back to the container 29 during the phase sample flow along pipe 33.

A mixing region 34 of the pipe is defined by a second pipe 35 adjoining pipe 33 in a generally "T" or "Y" shaped configuration. As solution is aspirated by the instrument pump system (for example, a nebuliser), an uncontrolled pressure drop is produced in pipe 35. This causes an uncontrolled flow of solution along pipe 33' from the mixing region 34. This flow rate is a combination of a controlled flow of solution from the syringe pump, and an uncontrolled flow of diluent along pipe 35. The inability to control the flow of diluent results in an uncontrolled dilution factor. There is no instrument pump to pump the diluted sample to the analyser in this arrangement.

Problems arise with systems which rely on this arrangement. For instance, there are limits to the dilution factor this system can provide, especially if the analyser requires the diluted sample to be pumped at a specific rate. This problem could be overcome by providing an instrument pump and pressure relief system, similar to that shown in FIG. 1. However, the problems associated with the system in FIG. 1 now become prevalent with this system, for example, diluent wastage.

U.S. Pat. No. 4,804,519 describes a sample analysis apparatus. A motor drives a pair of pumps with the same angular velocity, but different pump rates are achieved by using tubes with different internal diameter in each pump. This arrangement requires the tube of one or both of the pumps to be removed from the system whenever a different flow rate of solution through a pump is required.

U.S. Pat. No. 4,245,509 describes a sampling apparatus which uses syringe pumps to pump fluids through a mixing region. Each syringe is arranged so that each of the syringe's plungers are moved at the same rate. Thus, a difference in flow rates of fluid flowing from each syringe is only controlled by changing syringe diameter and/or tube diameter.

US 2002/0011437 A1 describes a liquid chromatograph system which controls a mixing ratio of two liquids by independently controlling the flow rate of two pumping devices, each of which pumps a different liquid, before the liquids reach a mixing region.

SUMMARY OF THE INVENTION

It is an aim of the present invention to ameliorate the problems associated with the prior art. Furthermore, it is an aim of the present invention to provide an apparatus which improves upon known systems in mass spectrometry. More specifically, there is provided a mass spectrometer pumping device for supplying a diluted sample to a mass spectrometric analyser, comprising: a mixer arranged to mix a sample with a diluent to form the diluted sample, said mixer being disposed between a first and a second conduit such that, in use, a sample enters the mixer through the first conduit at a first flow rate and a diluent enters the mixer through the second conduit at a second flow rate, the mixer being arranged so that said diluted sample exits the mixer through a third conduit at a third flow rate, said third flow rate being substantially equal to the sum of the first and second flow rates; pump means for pumping fluid through the mixer and into the analyser; and a pump controller arranged to receive data from the analyser indicative of the amount by which the sample is diluted and to control the pump means so that any of the first, second or third flow rates are adjustable with respect to one another in dependence upon the received data.

There is yet still provided a method for diluting a sample prior to performing mass spectrometry on the sample in an analyser, using a pump system comprising a first pump means, a diluent for diluting the sample, a mixer for mixing the sample and diluent, a first conduit disposed between a sample container and the mixer, a second conduit disposed between a diluent container and the mixer, and a third conduit disposed between the mixer and the analyser, wherein the pump means draws sample through the mixer, so that the flow rate of diluted sample along the third conduit is substantially the sum of the flow rate of diluent along the second conduit and the flow rate of sample along the first conduit, and a controller controls the pumps means to adjust the first, second or third flow rates with respect to one another in dependence upon data received from the analyser indicative of the amount by which the sample is diluted.

The embodiments have an advantage of reducing system complexity, increasing dilution factor range over which the system can operate acceptably, increasing sample throughput, and decreasing operator intervention. Providing a feedback of data from the analyser to the pump controller can provide near instantaneous automatic control of the amount by which the sample is diluted. This reduces the need for operator intervention, for instance, and can greatly improve the time efficiency of the analyser.

Embodiments of the present invention have a further advantage of a reduced number of pumps required to dilute the sample accurately before it is analysed with a substantial improvement to the range of dilution factors. The pump system and the dilution factor can be more easily controlled to better accuracy levels. The time taken to change samples for dilution is greatly reduced using embodiments of the present invention, thus increasing the number samples which might be tested by an analyser. Also, virtually no diluent is wasted during normal operation.

A further aspect of the present invention resides in the method further including: i) replacing the sample container with the another sample container containing a second sample: ii) varying the first rate to substantially the third rate for a predetermined time; and iii) after the predetermined time, reducing to first rate so that the sample is diluted by a dilution factor; wherein the predetermined time is substantially the time taken for the second sample to be transferred from the another container to the mixer at the first rate.

This further aspect has the advantage of substantially reducing the time taken to exchange samples for dilution and hence increases the number of samples which can be tested or analysed over a given time period.

The present invention provides an additional method for diluting a sample prior to performing mass spectrometry on the sample in an analyser, using a pump system comprising, a first pump means, a second pump means, a diluent for diluting the sample, a mixer for mixing the sample and diluent, a first pipe disposed between a sample container and the mixer, a second pipe disposed between a diluent container and the mixer, and a third pipe disposed between the mixer and the analyser, the first pump means being arranged to pump the sample or the diluent at a first or second flow rate along the first or second pipe respectively, to the mixer, the second pump means being arranged to pump the diluent or diluted sample at a second or third flow rate along the second or third pipe to the mixer or analyser respectively: the method comprising; a) pumping the diluted sample between the mixer and the analyser at the third rate; b) pumping the sample at an initial rate for a predetermined time; c) after the predetermined time, reducing the initial rate to the first rate; d) mixing the sample with a diluent to dilute the sample; and e) controlling the first or second pump means to adjust the first, second or third flow rates in dependence upon data received from the analyser indicative of the amount by which the sample is diluted, wherein, the initial rate is substantially the third rate, the predetermined time is the time taken for the sample to be transferred from the container to the mixer at the initial rate, and the third, second or first flow rate respectively is substantially equal to the difference between the second and first, third and first, or third and second flow rates respectively.

The present invention provides a yet further method supplying a diluted sample to a mass spectrometric analyser for analysis, comprising; diluting a sample by mixing said sample with a diluent in a mixer, pumping said diluted sample to the analyser from the mixer, and controlling the dilution factor by which the sample is diluted by controlling the flow rate of the sample and/or diluent to the mixer, wherein the controlling of the dilution factor step is carried out in response to data received by a pump controller from the analyser.

Embodiments of the invention have further advantages of substantially reducing the operator intervention, and increase the sample throughput rate. The embodiments aim to provide automated dilution of the sample at a consistent and safe level before the sample is introduced into the analyser. Dilution of the sample to a safe level also has the advantage of allowing the required precision of analysis to be carried out on trace levels within the sample by automatic dilution of the sample. The sample throughput can also be increased by a relatively rapid introduction of new (or different) sample solutions up to the mixing region by controlling the flow rate of the sample uptake. The cost of diluting samples can be reduced by reducing the amount of diluent used by the dilution system; only the volume of diluent required to dilute the sample to a required safe level can be consumed and little or no diluent is wasted. (By 'safe level', we mean a dilution factor necessary to avoid contamination of the analysis instrumentation.)

DESCRIPTION OF THE DRAWINGS

Embodiments of the present invention will now be described, by way of example, with reference to the accompanying drawings, in which:

FIG. 5 is a schematic diagram of a pump system that is another alternative embodiment of the pump system shown in FIG. 3; and FIG. 6 is a schematic diagram of a pump system that is yet another alternative embodiment of the pump system shown in FIG. 3.

DETAILED DESCRIPTION OF AN EMBODIMENT

Figure 1:
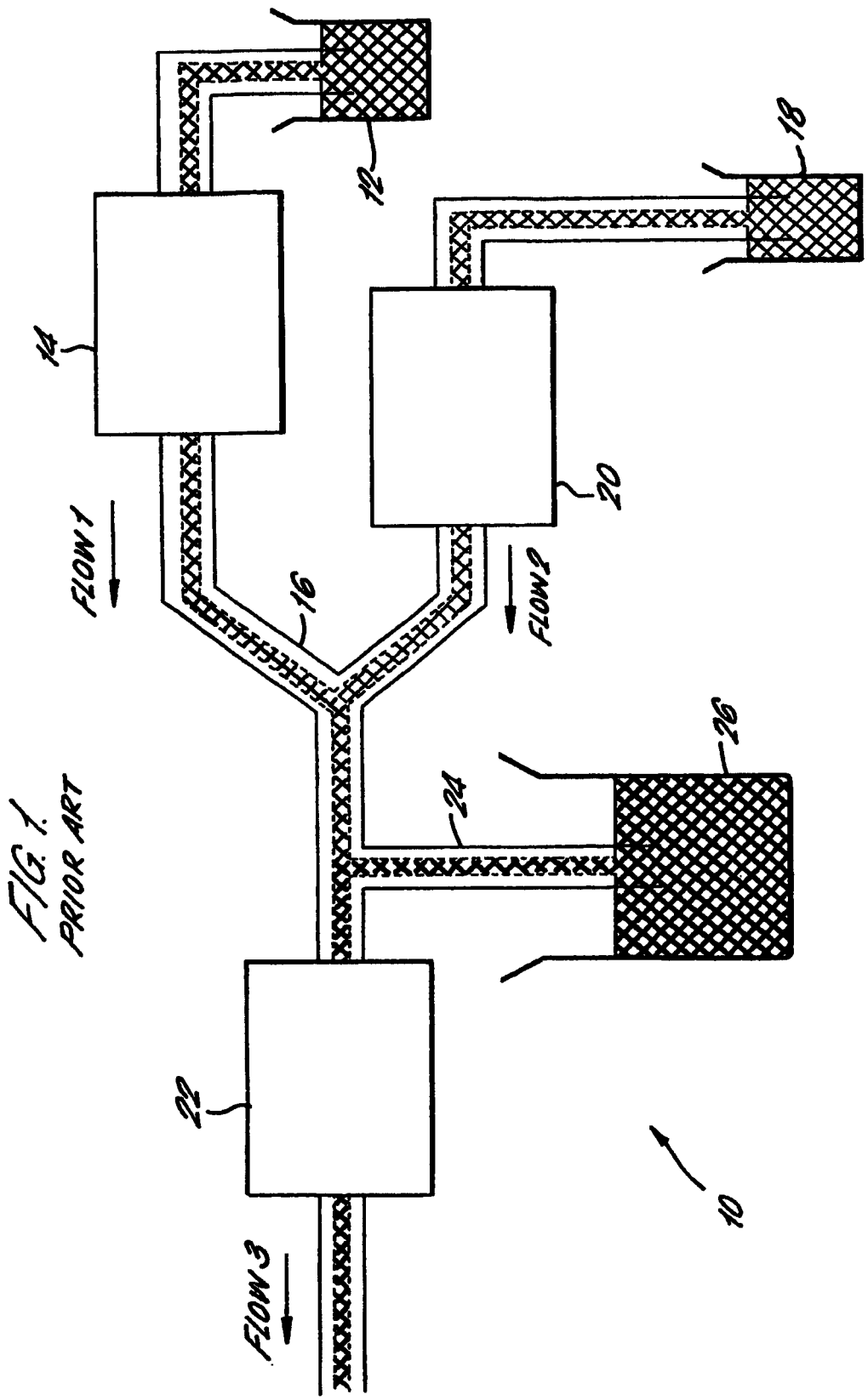
FIG. 1 is a schematic diagram of a pump system known in the art and described above.
Figure 2:
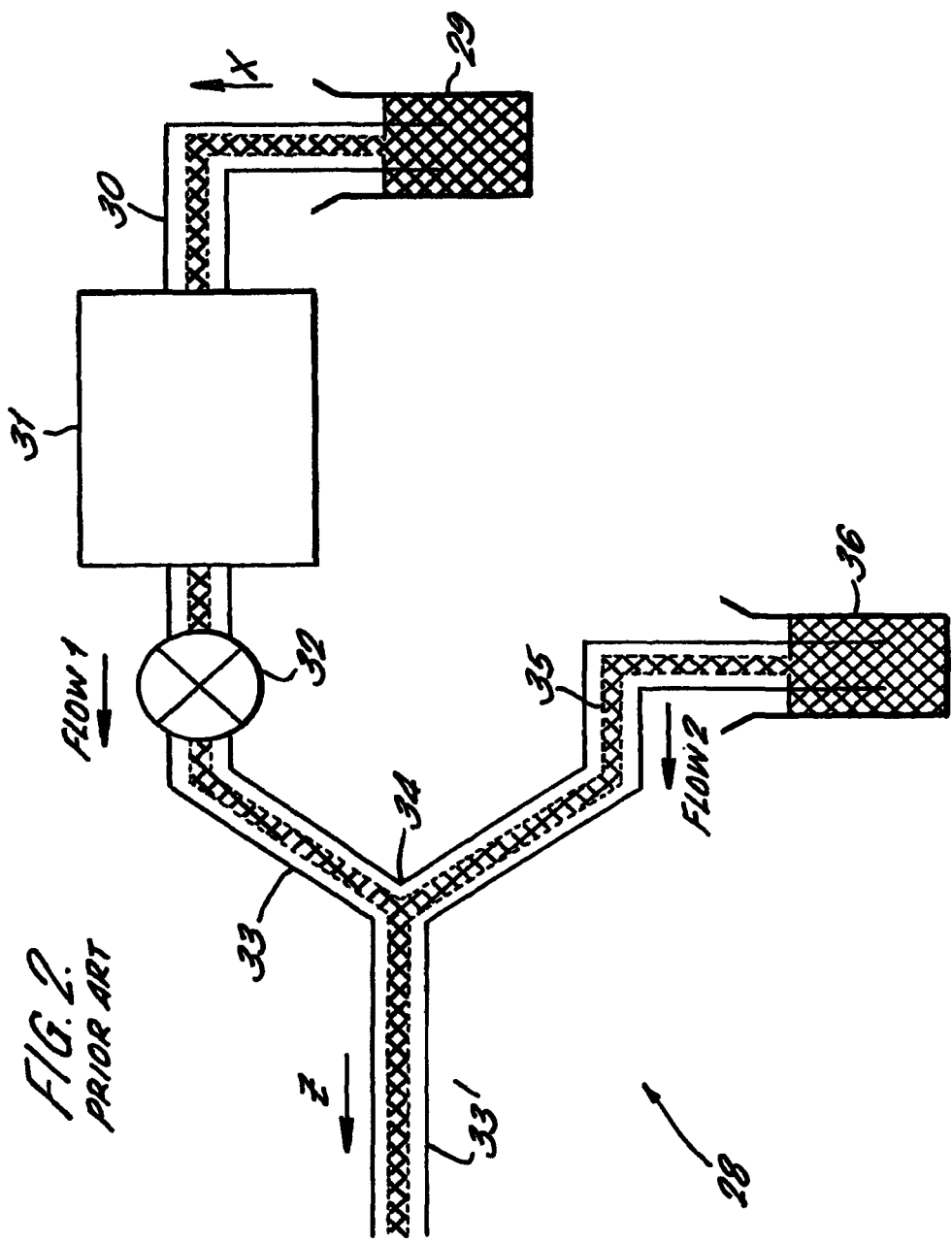
FIG. 2 is a schematic diagram of a pump system known in the art and described above.
Figure 3:
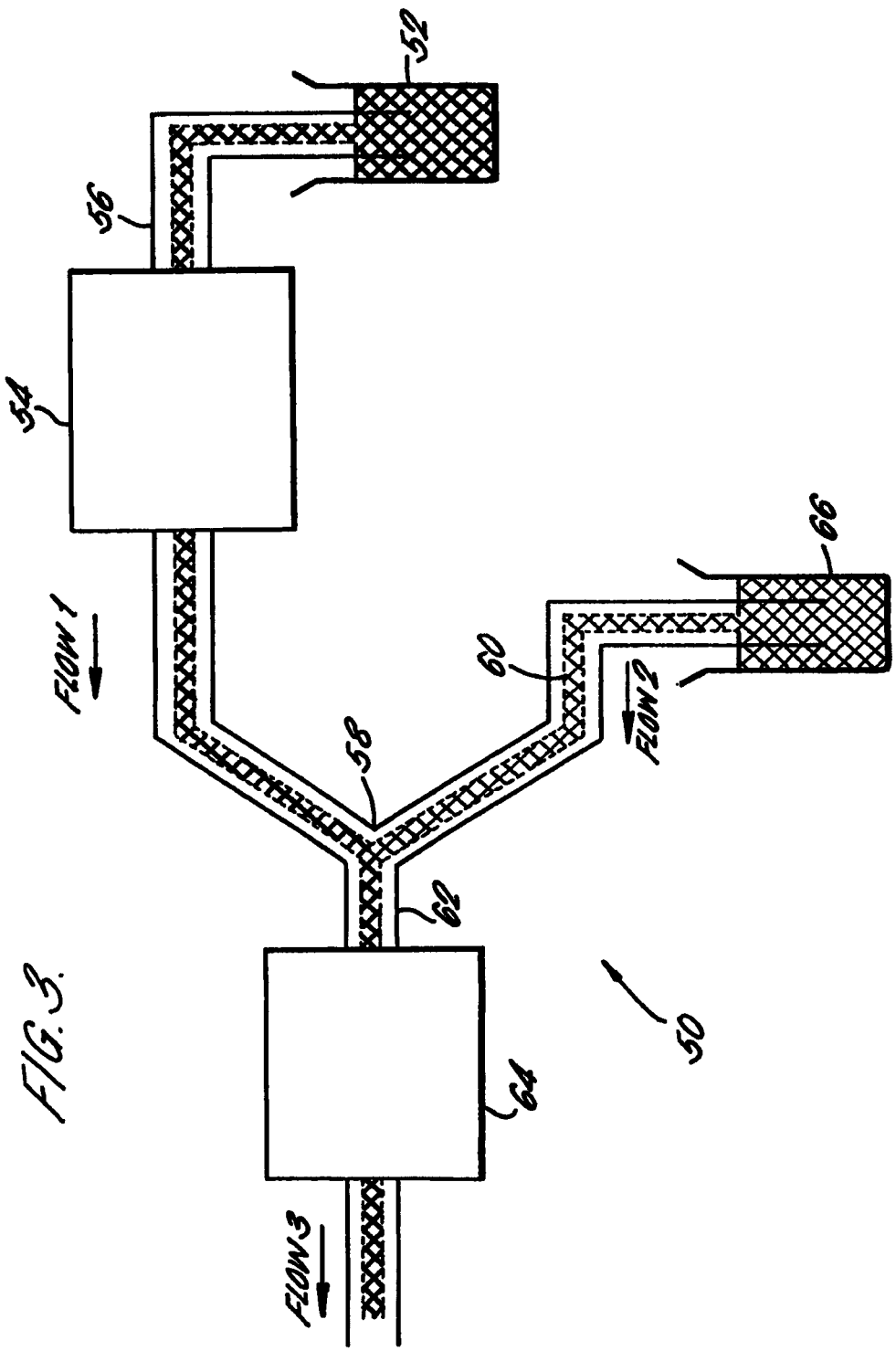
FIG. 3 is a schematic diagram of another pump system embodying the present invention.

Referring to FIG. 3, a pump system 50 embodying the present invention is shown in schematic form. A sample 52 to be analysed is drawn from a container by a first pump 54 along a first pipe 56 to a mixing section 58. The end of the first pipe at which the sample enters the system is completely submersed in the sample to ensure no air enters the system. At the mixing section, the first pipe 56 is joined to a second pipe 60 to form a single pipe 62.

The mixer is a "Y" or "T" configured junction in the tubing or pipes. Other, more complex arrangements of pipe joints might be used which ensure thorough mixing of the fluids entering the mixing region from the first and second pipes. The exit of the mixing section comprises a single pipe 62 disposed between the mixing section and a second pump 64 which pumps fluid from the mixing section to an instrument (not shown) for analysis.

Mixing of the sample and diluent to form a diluted sample takes place at the interface of the first, second and third pipes. Additional mixing might also occur for some length along the third pipe from the mixer to the analyser. Mixing occurs as a function of the turbulent flow of the sample and diluent at the junction and possibly along the third pipe, and also by diffusion of the two fluids. In this embodiment, mixing may also occur as the fluid passes through the second pump on the third pipe, particularly if the second pump is a peristaltic pump.

The first pump is preferably a piston type pump, similar to the milliGAT pump head supplied by Global FIA Inc. (described in U.S. Pat. No. 6,079,313). This type of pump allows a much greater range of flow rates, compared to peristaltic pumps for instance, and can operate to continuously pump relatively large or small volumes of sample at a constant, or varying flow rate, as desired. Furthermore, this type of pump can operate at very low flow rates (typically in the region of micro litres per minute) with the accuracy and precision required for ICPMS applications. This piston pump system does not suffer the disadvantages associated with the prior art systems described previously. The second pump may be the same type as the first pump, or, if appropriate, may be a (much cheaper) peristaltic pump. Of course, the first and second pumps are operable at different flow rates with respect to one another, and independently of each other.

A diluent 66 is drawn from a diluent container 67, up the second pipe 60 to the mixing section 58 where it mixes with the sample, and hence dilutes the sample. The end of the second pipe at which the diluent enters the system is completely submersed in the diluent to ensure air does not enter the system. The flow from the mixer to the instrument of the diluted sample is accurately controlled by the second pump 64 at Flow 3; the second pump is also controlled by the controller 55. Thus, when Flow 1<Flow 3, the diluent is drawn along the second pipe 60 to the mixer at a flow rate Flow 2, following the equation $$\text{Flow 1} + \text{Flow 2} = \text{Flow 3};$$

assuming the liquids in the pipes are non-compressible. (The flow can be measured in litres per minute).

Preferably, Flow 3 is kept constant by the second pump 64, hence the rate of arrival of diluted sample of the instrument is constant. Varying the flow rate of the first pump therefore changes the dilution factor D by which the sample is diluted, where $$D = \text{Flow 2}/\text{Flow 1, or}$$

$$D = (\text{Flow 3}/\text{Flow 1}) - 1.$$

So, from the equations above and assuming Flow 3 is constant, a decrease in the first pump's flow rate (Flow 1) increases the diluent flow to the mixer section, and hence the dilution factor D.

An example of how the pump system embodying the invention can operate with an ICP-MS instrument is now provided. During operation, all samples are routinely diluted by a discrete predetermined dilution factor $D_1$ before the sample is analysed. $D_1$ is initially set to a relatively high level so that the sample is diluted to such an extent that any dissolved solids (or matrix) in the sample are sufficiently diluted when the sample is analysed. In this way, adverse effects to the analysis instrumentation or the test result can be prevented or reduced. Typically, $D_1=100$.

Analysis software which checks the analyser results determines the extent of diluted matrix in the sample, to see whether further dilution is necessary. Also, the analysis data, or results are processed to determine the precision of the measured analyte signal. This data can be fed to the controller 55 for real time adjustment of the dilution factor, depending on the analysis results. For instance, if the analyte signal is too weak, the dilution factor may need to be reduced. Moreover, the instrument may not be able to measure analyte concentration with the required accuracy if the analyte signal is too intense (in which case the sample may require further dilution by a factor $D_2$). Flow rate information or data can be passed from the pumps (or any flow meters—not shown) back to the controller for use by the controller.

Therefore, it is possible for the controller to change the dilution factor (if necessary) having regard for the analyser results. For example, if the results show too much matrix remains in the diluted sample for accurate analysis, the controller can reduce the first pump's flow rate, thereby increasing the dilution factor, as described previously.

$D_2$ can be calculated by comparing the matrix signal from the analyser with a pre-determined maximum level used for providing adequately accurate results. As previously described, the new dilution factor $D_2$ is achieved by adjusting Flow 1 of the first pump 54. As a result, the dilution factor can be controlled in real time as analysis results are made available from the analyser. Thus the throughput of the instrument can be greatly improved and less intervention from a human operator is required. Furthermore, if the dilution factor is maintained at a relatively high level, the inlet of the analyser can be prevented from becoming contaminated with matrix materials, thus reducing the downtime necessary for cleaning the instrument.

When a new, or different, sample is required for analysis the first pump 54 pumps the new sample from a container at a rate just less than, or substantially equal to, Flow 3 for a period of T1. The period T1 is calculated so that the new sample completely fills the first pipe from the mixer 58 to the first pump 54, using the equation $$T1 = V/(\text{Flow 1})$$

where V is the volume of the tubing 56 from the sample uptake to the mixer, including any volume occupied by the sample within the first pump 54.

After time period T1 has elapsed the flow rate of the first pump is reduced, thus initiating dilution of the sample by a dilution factor, as previously described. The time taken for the diluted new sample to reach the analysis instrumentation can be calculated, knowing the volume of pipe from the mixer to the analysis instrument, including any volume occupied by the diluted sample in the second pump 64. Hence, the instrument can be programmed to start the analysis of the new sample only when the pump system has 'purged' itself of any previous samples which may have remained in the pumps or tubing.

In an alternative embodiment, the second pump is disposed between the diluent container and the mixing region. In this embodiment, the pump controller is capable of finely balancing the flow rate of each pump so that the flow of fluid to the analysis instrument remains constant. During the sample change over, or purge procedure described above, the instrument (or diluent) pump can be stopped until the new sample has been pumped to the junction in the mixer, at which point the diluent pump rate can be rapidly ramped up so that the new sample is diluted and pumped to the analyser for analysis. At the same time, the first flow rate is reduced so as to keep the flow to analyser constant.

A further embodiment includes an arrangement where the first pump is disposed on the second pipe with the second pump being between the mixer and the analyser.

Figure 4:
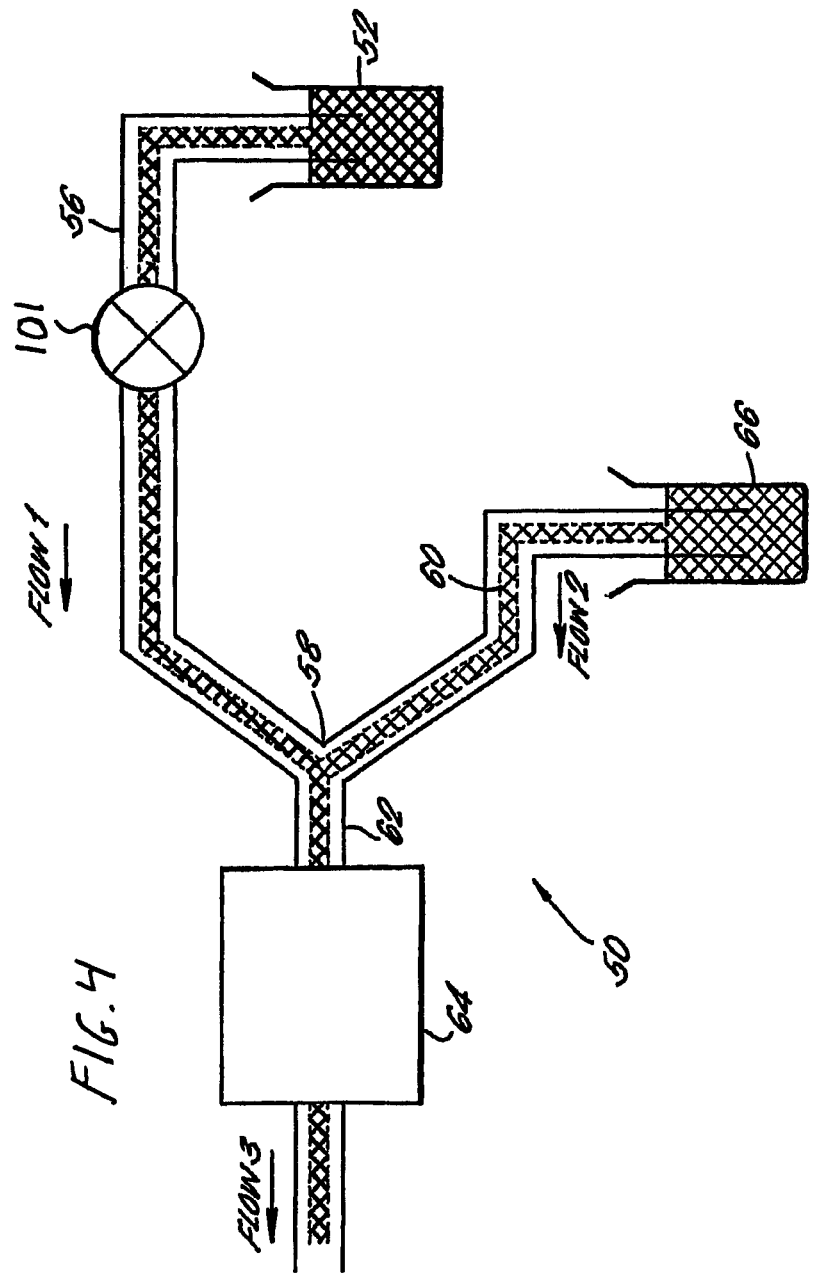
FIG. 4 is a schematic diagram of a pump system that is an alternative embodiment of the pump system shown in FIG. 3.

Another embodiment is provided by an arrangement where a single pump is disposed between the mixer and analyser and one, or both of the flow rates in the first or second pipe is controlled by at least one valve, or variable constriction. The valve, or valves, can be controlled by the pump controller, or a separate valve controller in communication with the pump controller. In this regard, FIG. 4 is a schematic diagram of a pump system that is an alternative embodiment of the pump system shown in FIG. 3. The pump system of FIG. 4 differs from the pump system of FIG. 3 in that, as discussed above, the pump 54 has been omitted in favor of a single pump 64, and a valve or variable constriction 101 is provided in the first pipe 56 to control the flow rate therethrough. FIG. 5 is a schematic diagram of a pump system that is another alternative embodiment of the pump system shown in FIG. 3. The pump system of FIG. 5 differs from the pump system of FIG. 3 in that, as discussed above, the pump 54 has been omitted in favor of a single pump 64, and a valve or variable constriction 102 is provided in the second pipe 60 to control the flow rate therethrough. FIG. 6 is a schematic diagram of a pump system that is yet another alternative embodiment of the pump system shown in FIG. 3. The pump system of FIG. 6 differs from the pump system of FIG. 3 in that, as discussed above, the pump 54 has been omitted in favor of a single pump 64, a valve or variable constriction 101 is provided in the first pipe 56 to control the flow rate therethrough, and a valve or variable constriction 102 is provided in the second pipe 60 to control the flow rate therethrough.

The pump systems described above are in a 'closed' configuration, by which we mean the sample and diluent are contained in the system from the input to the output; there is no waste pipe (as provided by the prior art). By keeping the system closed the equations above are maintained during operation. It is therefore important to make sure the diluent and the sample do not run out during operation to prevent air entering the system.

The tubing or pipe components of the pump system 50 should be made of suitably rigid materials to prevent expansion or contraction under any pressure. Such expansion or contraction is undesirable since it effects the volume V occupied by the sample, diluent and diluted sample. The expansion and contraction can be tolerated if their extent is determinable or predictable.

The mixer should preferably be designed to ensure full mixing of the sample and diluent by creating a turbulent flow in the mixing region of the pipe.

The first and second pumps should provide a substantially continuous flow, without any pulsing. The flow rate from each pump can be determined by using independent flow meters disposed fore or aft of the respective pump, with an appropriate feedback loop to the pump controller. Alternatively, the dilution factor can be measured using an internal standard. An appropriate software programme can be used by the controller to automate the dilution of the samples and change-over from one sample to the next, as described above. The controller might comprise a desktop PC with appropriate input and output devices to monitor and control the pumps, using an appropriate software programme.

An alternative method of determining the dilution factor can include "spiking" or "lacing" the sample solution with a known substance at a known concentration level. The spike is often referred to as an Internal Standard. Analysis of the analyser's results shows how much the sample has been diluted by the reduction of the level of known substance in the results. Of course, the known substances should be one which is not present in the sample or diluent before the spike is added. Such known substances might include Rhodium or Indium, for example.

To obtain very accurate dilution factor levels it is preferable to spike both the sample and the diluent. For example, the sample can be spiked with 100 parts per billion (ppb) concentration levels of Rhodium and 10 ppb of Indium. The diluent is not spiked with Rhodium, but is spiked with indium at a concentration level of 10 ppb. If the sample is diluted by, say, a factor of fifty, the Rhodium concentration is 2 ppb (after dilution). The Indium internal standard is still at a concentration level of 10 ppb as both the sample and diluent contain 10 ppb of indium.

However, the value of Rhodium concentration varies if there is an instability in the dilution (such instability might be caused by an air bubble in the mixer, or by inconsistent mixing of sample with the diluent, for example). In the case of an air bubble passing through the system, the Rhodium concentration levels might read 1.2 ppb, followed by 1.99 ppb on the next batch and 2.0 ppb on the last batch. This leads to a mean value of 1.73 ppb, or a 13.5% error of the expected dilution factor of 50:1. A correction for each batch can be made by scaling the values for each batch; the scaling factor for the first batch would be 2/1.2, the scaling factor for the second batch would be 2/1.99 and the scaling factor for the third batch would be 2/2.0. This can eliminate any errors in perceived concentration levels of the sample, which would otherwise be in error had the anomaly in the dilution factor not been noticed. This spiking, or use of an internal standard, allows for dilutions in excess of 50:1 without the risk of micro-bubbles or mixing effects causing errors in data.

Furthermore, spiking the diluent and sample with Indium having the same levels of concentration is advantageous, particularly in a situation where the sample is pumped to the mixer and fluid in the mixer is pumped to the instrument, but diluent is not actively pumped to the mixer (i.e., there is no pump on the line between the diluent vessel and the mixer, so the flow of diluent is related to the relative flows of the sample pump and instrument pump). Problems can arise when a zero dilution factor is required. To achieve zero dilution, both the instrument and sample pumps should run with the same flow rates. However, if the sample pump is running slightly faster than instrument pump, then a portion of the sample is forced into the diluent, contaminating the diluent. It is therefore preferable to run the sample pump with a flow rate of the order of 10% less than the instrument pump's flow rate. This way the sample is only slightly diluted. Detecting the concentration levels of Rhodium can account for, or determine this small dilution factor.

The indium spike can also be used to detect and/or determine any variations which might occur in the sample ionisation process. In the case of ICP-MS the ionisation occurs in a plasma torch, and variations in the torch's consistency or plasma condition can be detected by the levels of indium detected in the mass spectrum. This is so because indium concentration levels should always be 10 ppb, but if less than this concentration is detected then a correction can be made to factor into the result inconsistencies in ion formation, for instance.

Embodiments of the present invention can be used with an automated sample dispenser, or the like.

Examples of samples used by embodiments of the present invention include drinking water, waste water, sea water, dilute acids, urine, blood, spinal fluid, dissolved solid or gaseous samples, or the like. These examples are by no means exclusive, and any liquid sample which requires analysis can be diluted prior to entering the analyser by a system which embodies the present invention. Of course, an appropriate diluent is required for different samples and the choice of diluent for a given sample does not form part of the present invention. The diluent may be de-ionised water, ethanol or the like, but whatever is most suitable depending on the sample being analysed.

Further embodiments of the present invention will be envisaged by the skilled person. For example, the embodiments have been described using in-line pumps, but it may be desirable to use other pumping systems.

What is claimed:

1. A method of diluting a sample for performing trace element spectrometry analysis of the sample, the sample comprising one or more trace elements and matrix, the method comprising the steps of:
   a) diluting a portion of the sample by a dilution factor;
   b) analyzing the diluted portion of the sample to determine a matrix level in the diluted portion of the sample; and
   c) adjusting the dilution factor to be used when diluting the remainder of the sample based on a comparison between the determined matrix level and a pre-determined matrix level.

2. The method of claim 1, wherein the adjusting step is based on a comparison between the determined matrix level and a pre-determined maximum matrix level.

3. The method of claim 2, wherein the adjusting step comprises increasing the dilution factor if the determined matrix level is above the pre-determined maximum matrix level.

4. The method of claim 2, wherein the pre-determined maximum matrix level is 2000 mg/l.

5. The method of claim 2, wherein the adjusting step comprises decreasing the dilution factor if the determined matrix level is below the pre-determined maximum matrix level.

6. The method of claim 1, wherein the diluting step comprises diluting the sample by a first dilution factor and the adjusting step comprises adjusting the first dilution factor to a second dilution factor based on the determined matrix level.

7. The method of claim 6, wherein the first dilution factor is 100.

8. The method of claim 6, wherein the second dilution factor is calculated by comparing the determined matrix level with a pre-determined maximum matrix level.

9. The method of claim 1, wherein the adjusting step comprises adjusting a flow rate of a diluent relative to a flow rate of the sample upstream of a mixing region for providing the diluted sample.

10. The method of claim 1, wherein the analyzing step comprises mass analyzing the diluted sample with a mass spectrometer.

11. The method of claim 10, wherein the mass spectrometer comprises an inductively coupled plasma mass spectrometer.

12. The method of claim 1, wherein the dilution factor is controlled in real time as the matrix level is determined by the analyzing step.

13. A method of diluting a sample for spectrometry analysis comprising:
- a) taking a portion of the sample comprising one or more trace elements and matrix;
- b) diluting a portion of the sample;
- c) measuring a concentration of the matrix in the diluted sample;
- d) controlling the dilution of the remainder of the sample based on a comparison between the matrix concentration signal measured from the previously diluted portion of the sample and a pre-determined matrix concentration level.

14. A sample dilution device in combination with an analyzer, the sample dilution device for supplying a diluted sample to the analyzer for spectrometry analysis thereof, the diluted sample comprising one or more trace elements and matrix, wherein:
- a) the device comprises a first structure configured to dilute a first portion of a sample by a dilution factor;
- b) the analyzer is configured to receive and analyze the diluted portion of the sample and determine a matrix level in the diluted portion of the sample; and
- c) the device further comprises a device controller comprising data related to a predetermined matrix level, the device controller configured to receive data from the analyzer which is related to the determined matrix level in the diluted portion of the sample and configured to control the dilution of the remainder of the sample based on a comparison between the determined matrix level and the pre-determined matrix level by adjusting the dilution factor based on the comparison between the determined matrix level and the pre-determined matrix level.

15. The device of claim 14, wherein the device controller is arranged to compare the determined matrix level with a pre-determined maximum matrix level and to adjust the dilution factor for the sample based on the comparison.

16. The device of claim 15, wherein the device controller is arranged to increase the dilution factor if the determined matrix level is above the pre-determined maximum matrix level.

17. The device of claim 15, wherein the pre-determined maximum matrix level is 2000 mg/l.

18. The device of claim 15, wherein the device controller is arranged to decrease the dilution factor if the determined matrix level is below the pre-determined maximum matrix level.

19. The device of claim 14, wherein the device controller is arranged to dilute the sample by a first dilution factor and to adjust the first dilution factor to a second dilution factor based on the determined matrix level.

20. The device of claim 19, wherein the first dilution factor is 100.

21. The device of claim 19, wherein the device controller is arranged to calculate the second dilution factor by comparing the determined matrix level with a pre-determined maximum matrix level.

22. The device of claim 14, wherein the device controller is arranged to adjust a flow rate of a diluent relative to a flow rate of the sample upstream of a mixing region for providing the diluted sample.

23. The device of claim 14, further comprising a mass spectrometer for mass analyzing the diluted sample to provide the data comprising the determined matrix level to the device controller.

24. The device of claim 23, wherein the mass spectrometer comprises an inductively coupled plasma mass spectrometer.

25. The device of claim 14, wherein the device controller is arranged to control the dilution of the sample in real time as the matrix level is determined from the received data from the analyzer.

26. A non-transitory computer-readable medium on which is stored a computer program comprising instructions which, when run on a computer, cause the computer to carry out the method of claim 1.

* * * * *